(12) United States Patent
Oexman et al.

(10) Patent No.: US 8,813,285 B2
(45) Date of Patent: *Aug. 26, 2014

(54) APPARATUSES AND METHODS PROVIDING VARIABLE SUPPORT AND VARIABLE COMFORT CONTROL OF A SLEEP SYSTEM AND AUTOMATIC ADJUSTMENT THEREOF

(71) Applicant: Kingsdown, Inc., Mebane, NC (US)

(72) Inventors: Robert D. Oexman, Carthage, MO (US); David B. Scott, Hurdle Mills, NC (US)

(73) Assignee: Kingsdown, Inc., Mebane, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/712,351

(22) Filed: Dec. 12, 2012

(65) Prior Publication Data

US 2013/0174347 A1    Jul. 11, 2013

Related U.S. Application Data

(63) Continuation of application No. 12/867,690, filed as application No. PCT/US2008/083620 on Nov. 14, 2008, now Pat. No. 8,341,786.

(60) Provisional application No. 61/028,591, filed on Feb. 14, 2008.

(51) Int. Cl.
| | |
|---|---|
| A61B 5/00 | (2006.01) |
| A47C 31/12 | (2006.01) |
| A47C 23/047 | (2006.01) |
| A47C 27/08 | (2006.01) |
| A47C 23/043 | (2006.01) |
| A47C 27/10 | (2006.01) |

(52) U.S. Cl.
CPC ............. *A47C 27/083* (2013.01); *A47C 31/123* (2013.01); *A47C 23/047* (2013.01); *A47C 23/0433* (2013.01); *A47C 27/082* (2013.01); *A47C 27/10* (2013.01); *A47C 23/0435* (2013.01); *A47C 27/088* (2013.01)
USPC .................................. 5/713; 700/301; 5/655.3

(58) Field of Classification Search
CPC .... A47C 31/123; A47C 27/10; A47C 27/082; A47C 27/083
USPC ............ 5/614, 665, 713, 655.3, 727; 700/301
See application file for complete search history.

(56) References Cited

U.S. PATENT DOCUMENTS

| | | | |
|---|---|---|---|
| 3,462,778 | A | 8/1969 | Whitney |
| 3,786,676 | A | 1/1974 | Korolyshun et al. |

(Continued)

FOREIGN PATENT DOCUMENTS

| | | |
|---|---|---|
| GB | 2373189 A | 9/2002 |
| JP | H 6-315424 A | 11/1994 |

(Continued)

OTHER PUBLICATIONS

European Search Report dated Sep. 9, 2011.

(Continued)

*Primary Examiner* — Michael D Masinick
(74) *Attorney, Agent, or Firm* — Sughrue Mion, PLLC (57) ABSTRACT

An apparatus and method providing variable support and variable comfort control of a sleep system, the apparatus including a sleep support member including: a comfort layer including: a plurality of comfort layer inflatable members; and a comfort layer sensor configured to provide data relating to respective pressures of the comfort layer inflatable members; a data analysis unit configured to analyze data provided by the comfort layer sensor and to generate analyzed comfort layer data; and a control unit configured to control a pressure within each of the respective comfort layer inflatable members using the analyzed comfort layer data.

17 Claims, 7 Drawing Sheets

(56) References Cited

U.S. PATENT DOCUMENTS

| | | | |
|---|---|---|---|
| 4,466,385 A | 8/1984 | Waryasz | |
| 4,501,034 A | 2/1985 | Greenawalt | |
| 4,656,334 A | 4/1987 | Endo et al. | |
| 4,982,466 A | 1/1991 | Higgins et al. | |
| 5,020,176 A | 6/1991 | Dotson | |
| 5,062,169 A | 11/1991 | Kennedy et al. | |
| 5,105,488 A * | 4/1992 | Hutchinson et al. | 5/710 |
| 5,148,706 A | 9/1992 | Masuda et al. | |
| 5,231,717 A | 8/1993 | Scott et al. | |
| 5,283,735 A | 2/1994 | Gross et al. | |
| 5,446,933 A | 9/1995 | Gabelhouse | |
| 5,625,914 A | 5/1997 | Schwab | |
| 5,636,396 A * | 6/1997 | Workman et al. | 5/717 |
| 5,848,450 A | 12/1998 | Oexman et al. | |
| 5,850,644 A | 12/1998 | Hsia | |
| 5,948,303 A | 9/1999 | Larson | |
| 5,963,997 A | 10/1999 | Hagopian | |
| 5,987,675 A | 11/1999 | Kim | |
| 5,989,258 A | 11/1999 | Hattori | |
| 6,008,598 A | 12/1999 | Luff et al. | |
| 6,212,718 B1 | 4/2001 | Stolpmann et al. | |
| 6,220,088 B1 | 4/2001 | Scales et al. | |
| 6,226,792 B1 | 5/2001 | Goiffon et al. | |
| 6,269,505 B1 | 8/2001 | Wilkinson | |
| 6,327,725 B1 | 12/2001 | Veilleux et al. | |
| 6,384,715 B1 | 5/2002 | Potter | |
| 6,421,858 B1 | 7/2002 | Cuerel | |
| 6,468,234 B1 | 10/2002 | Van der Loos et al. | |
| 6,560,803 B2 | 5/2003 | Zur | |
| 6,571,192 B1 | 5/2003 | Hinshaw et al. | |
| 6,585,328 B1 | 7/2003 | Oexman et al. | |
| 6,662,393 B2 | 12/2003 | Boyd | |
| 6,687,935 B2 | 2/2004 | Reeder et al. | |
| 6,741,950 B2 | 5/2004 | Hinshaw et al. | |
| 6,878,121 B2 | 4/2005 | Krausman et al. | |
| 6,916,236 B2 | 7/2005 | Terpstra | |
| 6,986,182 B2 * | 1/2006 | Mossbeck | 5/727 |
| 6,990,425 B2 | 1/2006 | Hinshaw et al. | |
| 7,036,172 B2 | 5/2006 | Torbet et al. | |
| 7,127,759 B2 | 10/2006 | Koops | |
| 7,685,658 B2 | 3/2010 | Lokhorst et al. | |
| 7,725,967 B2 | 6/2010 | Simmerer et al. | |
| 7,764,180 B2 | 7/2010 | Huang | |
| RE41,809 E | 10/2010 | Hinshaw et al. | |
| 7,877,827 B2 | 2/2011 | Marquette et al. | |
| 8,122,546 B2 | 2/2012 | Chambers et al. | |
| 2003/0125899 A1 | 7/2003 | Hinshaw et al. | |
| 2003/0208848 A1 * | 11/2003 | Flick et al. | 5/713 |
| 2004/0139549 A1 | 7/2004 | Mohrekesh et al. | |
| 2004/0177449 A1 * | 9/2004 | Wong et al. | 5/713 |
| 2004/0215416 A1 | 10/2004 | Hinshaw et al. | |
| 2005/0143617 A1 | 6/2005 | Auphan | |
| 2005/0166326 A1 | 8/2005 | Chaffee | |
| 2006/0112489 A1 | 6/2006 | Bobey et al. | |
| 2006/0143831 A1 | 7/2006 | Wu | |
| 2006/0179573 A1 | 8/2006 | Nissen et al. | |
| 2006/0236460 A1 | 10/2006 | Hooper | |
| 2007/0021965 A1 | 1/2007 | Boyd | |
| 2007/0056112 A1 | 3/2007 | Graebe | |
| 2007/0061974 A1 | 3/2007 | Gabbay | |
| 2007/0061976 A1 | 3/2007 | Bazargani | |
| 2007/0086947 A1 | 4/2007 | Boyd | |
| 2007/0199154 A1 | 8/2007 | Escaross | |
| 2007/0227594 A1 | 10/2007 | Chaffee | |
| 2007/0238935 A1 | 10/2007 | Boyd | |
| 2008/0244831 A1 | 10/2008 | Kenmochi | |
| 2008/0307582 A1 * | 12/2008 | Flocard et al. | 5/712 |
| 2009/0006027 A1 | 1/2009 | Hinshaw | |
| 2009/0240514 A1 | 9/2009 | Oexman et al. | |
| 2010/0313359 A1 | 12/2010 | Scott et al. | |
| 2010/0317930 A1 | 12/2010 | Oexman et al. | |
| 2011/0010014 A1 | 1/2011 | Oexman et al. | |
| 2011/0010249 A1 | 1/2011 | Oexman et al. | |
| 2011/0163885 A1 | 7/2011 | Poulos et al. | |

FOREIGN PATENT DOCUMENTS

| | | |
|---|---|---|
| JP | 2000-189472 A | 7/2000 |
| WO | 9732509 A1 | 9/1997 |
| WO | 9963314 A1 | 12/1999 |
| WO | 0051470 A1 | 9/2000 |
| WO | 2005104904 A1 | 11/2005 |
| WO | 2006023479 A2 | 3/2006 |
| WO | 2007053150 A1 | 5/2007 |

OTHER PUBLICATIONS

Diffrient, Niels et al., Humanscale 1/2/3, 1974, The MIT Press, Cambridge.

Diffrient, Niels et al., Humanscale 4/5/6, 1981, The MIT Press, Cambridge.

Tilley, Alvin R., The Measure of Man and Woman, 2002, John Wiley & Sons, New York.

Jacobson, Bert H. et al., "Subjective Rating of Perceived Back Pain, Stiffness and Sleep Quality Following Introduction of Medium-Firm Bedding Systems," Journal of Chiropractic Medicine, Winter 2006, pp. 128-134, vol. 5, No. 4, National University of Health Sciences.

Iber, Conrad et al., The AASM Manual for the Scoring of Sleep and Associated Events: Rules, Terminology and Technical Specifications, 1st ed., 2007, American Academy of Sleep Medicine, Westchester, Illinois.

Dement, William C., "History of Sleep Physiology and Medicine," in Principles and Practice of Sleep Medicine, eds. Meir H. Kryger, Thomas Roth, and William C. Dement, 4th Edition, 2005, Elsevier Inc., Philadelphia.

Raymann et al., "Skin Deep: Enhanced Sleep Depth by Cutaneous Temperature Manipulation," Brain: A Journal of Neurology, 2008, pp. 500-513, vol. 131, Oxford University Press.

European Search Report dated Sep. 12, 2011 for EP08872303.6.

Russian Office Action dated Jun. 8, 2011 for RU 2010135586.

Singapore Patent Office Action dated Feb. 27, 2012 for SG 201005897-2.

International Search Report dated Apr. 10, 2012 for PCT/US2011/050122.

Office Action issued Nov. 7, 2013, in U.S. Appl. No. 12/919,189.

Chinese Office Action dated Dec. 4, 2013 for Chinese application 200880128584.3.

Notice of Allowance dated Feb. 20, 2014 issued for U.S. Appl. No. 12/919,189.

Office Action mailed May 29, 2014 for Korea application 10-2010-7020337.

* cited by examiner

APPARATUSES AND METHODS PROVIDING VARIABLE SUPPORT AND VARIABLE COMFORT CONTROL OF A SLEEP SYSTEM AND AUTOMATIC ADJUSTMENT THEREOF

CROSS-REFERENCE TO RELATED PATENT APPLICATION

This is a Continuation of application Ser. No. 12/867,690 filed Aug. 13, 2010, which is a National Stage Entry of PCT/US2008/083620 filed Nov. 14, 2008, which claims priority from U.S. Provisional Application No. 61/028,591, filed on Feb. 14, 2008, in the U.S. Patent and Trademark Office, the disclosures of which are incorporated herein by reference in their entirety.

BACKGROUND

1. Technical Field

Apparatuses and methods consistent with the present invention relate to sleep systems that provide variable control of the support and comfort characteristics of the sleep system. More particularly, these apparatuses and methods provide automatic adjustment of the support and comfort characteristics of a sleep system based on a person's body variances. These apparatuses and methods also provide manual adjustment of the support and comfort characteristics of the sleep system based on support and comfort levels that a person selects.

2. Description of the Related Art

A wide variety of different sleep systems are currently available. Such sleep systems may comprise all aspects of a bedding assembly including, but not limited to, mattresses, box springs, foundation units, bed frames, pillows, mattress pads, linens and, more generally, to any type of sleep product that influences a person's sleep. However, each respective sleep system may be suitable for some persons but not suitable for others persons. The characteristics of a suitable sleep system for a person depend on a number of factors including, but not limited to, the physical attributes of the person (e.g., weight, height, body dimensions, weight distribution, etc.), preferred sleeping positions (e.g., sleeping on back, side, front, etc.), sleeping habits and so on.

Two very different primary components of sleep systems affect a person's overall sleep experience: support and comfort. First, a sleep system delivers support to a person by holding the person in a proper postural alignment, while evenly redistributing the person's body weight across a wide area so as to relieve interface pressure. For example, a mattress may deliver support through the resistance provided by innersprings to the downward force applied due to the person's body weight.

Second, a sleep system delivers comfort to a person's body through the use of comfort materials layered on a top region of the sleep surface. For instance, by layering firming pads and harder, high density foam on top of the innersprings, a mattress can be manufactured to provide varying levels of hardness or firmness. On the other hand, by layering soft materials over the innersprings like convoluted foam, low density foam and/or fiber materials like wool, silk or cashmere, a mattress can be manufactured to provide varying levels of softness or a more plush feel.

The sleep system that is most suitable for a particular person is that sleep system which provides the best possible combination of comfort and support to the person. Further, suitable sleep systems will vary considerably based on a person's physical attributes, sleeping habits, etc.

The number of factors that influence the suitability of a sleep system for a person are vast and interrelated. Thus, the selection of a suitable sleep system can be a complicated and difficult process for a person. Further, the sleep system that a person selects for themselves based on what sleep system feels most appealing to the person during a showroom testing of the sleep system may not be the most suitable sleep system for the person. Rather, it may require several weeks of sleeping on a given sleep system for a person to determine the long-term suitability of the sleep system. However, prospective sleep system purchasers are generally limited to such brief showroom testing.

Apparatuses and methods for objectively evaluating a person on a sleep system so as to determine the optimal comfort and support characteristics for the person have been developed by the inventors of the present application, as set forth in a related Provisional Application entitled "Apparatus and Methods for Evaluating a Person on a Sleep System," which is incorporated by reference in its entirety. The apparatuses and methods disclosed in the aforementioned related Provisional Application can be employed to (among other things) recommend which of the generic sleep systems that are commercially available will most closely provide the person with the optimal comfort and support characteristics that are determined for the person based on their individual characteristics. Thus, apparatuses and methods disclosed in the aforementioned related Provisional Application (among other things) assist a purchaser in determining the long-term suitability of a sleep system during a brief showroom setting.

However, conventionally, purchasers are typically limited to selecting one of the limited models of generic sleep systems that are commercially available. But, the limited number of generic sleep systems that are commercially available may not precisely provide the optimal comfort and support characteristics that are determined for the person according to the apparatuses and methods of the aforementioned related Provisional Application since generic sleep systems are not custom manufactured to the purchaser's individual characteristics.

Thus, there is a need for a sleep system that can be precisely varied to provide custom determined optimal comfort and support characteristics for a person based on that person's individual characteristics.

Additionally, during the course of a night, a person will experience numerous body variances. For example, among other body variances, the person will exhibit movement and the person's sleeping position will vary throughout the night. The person's heart rate, rate of breathing, state of sleep and sleep quality will also vary. As the person experiences such variances over the course of the night, the optimal sleep system support and comfort characteristics corresponding to the experienced variances will also vary.

However, the support and comfort characteristics of conventional mattresses (even adjustable mattresses) are fixed and do not vary automatically while a person sleeps. Thus, there is a need for a sleep system that can detect and analyze a person's body variances. There is also a need for a sleep system that can automatically adjust the support and comfort characteristics of the sleep system based on such body variances on an immediate basis.

It is also important to recognize that a person's physical attributes (e.g., weight, weight distribution, etc.) and sleeping habits may vary somewhat over time after the person purchases a particular sleep system. For example, the person may gain or loose substantial weight over time, or the person's preferred sleeping position may change. Consequently, the optimal sleep system support and comfort characteristics corresponding to the person's physical attributes may also vary over time. Thus, there is a need for a sleep system that can analyze such long-term variances and automatically adjust its support and comfort characteristics over time, on a weekly or nightly basis, for example.

Further, a person's support and comfort preferences may vary and, thus, there is a need for a sleep system which allows a person to manually adjust its support and comfort characteristics to the person's liking.

Conventional mattresses have failed to adequately address the above needs and other needs not explicitly mentioned above. For example, a pocketed coil type mattress designed to have an adjustable level of support is described in U.S. Pat. No. 6,986,182 (hereinafter "the '182 patent), which is incorporated herein by reference in its entirety. The support level adjustment mechanism described regarding that conventional adjustable mattress uses several air bladders that are placed under individual pocketed coils of the mattress.

However, the mattress described in the '182 patent has numerous disadvantages. For example, although the conventional mattress described in the '182 patent can change the amount or level of support, it cannot not adjust for comfort.

Further, according to the mattress described in the '182 patent, each of the air bladders is of a width equal to one of the strings of springs. More particularly, as shown in FIGS. 1, 2 and 4 of the '182 patent, the mattress described therein has a number of coil springs 34, each coil spring being contained within a fabric pocket 32. Each of a plurality of inflatable pneumatic members 50 are arranged underneath a respective row of the pocketed coil springs. The inflatable pneumatic members 50 are connected to an air pump 64 through pneumatic tubes 62 and 60. When the air pump 64 supplies air to the inflatable pneumatic members 50, the inflatable pneumatic members 50 expand. When air is released from the inflatable pneumatic members 50, the inflatable pneumatic members 50 contract.

In the mattress described in the '182 patent, each of the inflatable pneumatic members 50 is placed directly underneath a single row of pocketed coil springs, as clearly shown in FIG. 3 of the '182 patent. Thus, when a respective inflatable pneumatic member 50 is inflated so that it expands, the respective inflatable pneumatic member 50 operates to compress only the single row of pocketed coil springs that is located directly above it.

By compressing the pocketed coil springs, the pocketed coil springs provide firmer support in the specific area of the mattress where the single row of pocketed coil springs is located. When air is released from an inflatable pneumatic member 50, the inflatable pneumatic member 50 compresses, as shown, for example, in FIG. 6 of the '182 patent, by inflatable pneumatic member 50c. This allows the row of pocketed coil springs above the inflatable pneumatic member 50c to decompress, thereby providing less support in those areas of the mattress where the row of pocketed coil springs is located.

However, the mattress described in the '182 patent only provides an adjustable level of support. It does not allow for adjusting a degree of comfort for the person. Further, the mattress described in the '182 patent can only provide a minimal overall increase in support. For example, indentation load deflection tests performed on the mattress described in the '182 patent show an overall increase in support that is a fraction of the illustrative embodiments described herein. The mattress described in the '182 patent also does not automatically adjust the support and comfort characteristics of the sleep system based on the person's body variances.

Thus, there is a need for a sleep system having variable comfort characteristics in addition to an adjustable degree of support provided by the sleep system and for a sleep system that provides automatic adjustment, as described above. There is also a need for a sleep system in which the force applied by each inflatable member is dispersed among a plurality of rows of coils, rather than being limited to the single row of coils directly above it.

SUMMARY

Aspects of the present invention provide a sleep system having variable control of the support and comfort characteristics of the sleep system. Aspects of the present invention also provide automatic adjustment of the support and comfort characteristics of a sleep system in response to a person's body variances. Further, aspects of the present invention provide manual adjustment of the support and comfort characteristics of a sleep system based on support and comfort levels that a person selects.

An aspect of the present invention provides a sleep system comprising: a sleep support member comprising: a comfort layer comprising: a plurality of comfort layer inflatable members; and a comfort layer sensor configured to provide data relating to respective pressures of the comfort layer inflatable members; a data analysis unit configured to analyze data provided by the comfort layer sensor and to generate analyzed comfort layer data; and a control unit configured to control a pressure within each of the respective comfort layer inflatable members using the analyzed comfort layer data.

Another aspect of the present invention provides a sleep system comprising: a sleep support member comprising: a support layer comprising: a plurality of support layer inflatable members; and a support layer sensor configured to provide data relating to respective pressures of the support layer inflatable members; a data analysis unit configured to analyze data provided by the support layer sensor and to generate analyzed support layer data; and a control unit configured to control a pressure within each of the respective support layer inflatable members using the analyzed support layer data.

Another aspect of the present invention provides a method of controlling a variable sleep support member, the method comprising: determining whether a person is disposed on the sleep support member; if a person is disposed on the sleep support member, then: analyzing data relating to respective pressures of a plurality of comfort layer inflatable members that are arranged in a comfort layer of the sleep support member to generate analyzed comfort layer data; and controlling a pressure within at least one of the comfort layer inflatable members using the analyzed comfort layer data.

BRIEF DESCRIPTION OF THE DRAWINGS

The above and other aspects of the present invention will become more apparent by describing in detail illustrative embodiments thereof with reference to the attached drawings in which.

DETAILED DESCRIPTION OF ILLUSTRATIVE EMBODIMENTS

Illustrative embodiments of the invention will now be described in detail with reference to the attached drawings in which like reference numerals refer to like elements.

Aspects of the present invention provide a method and apparatus for adjusting the support and comfort characteristics that a sleep system provides. The support and comfort characteristics of the illustrative sleep system may be adjusted automatically in response to a person's body variances. On the other hand, the support and comfort characteristics of the sleep system may be adjusted manually based on support and comfort levels that a person selects.

Figure 1:
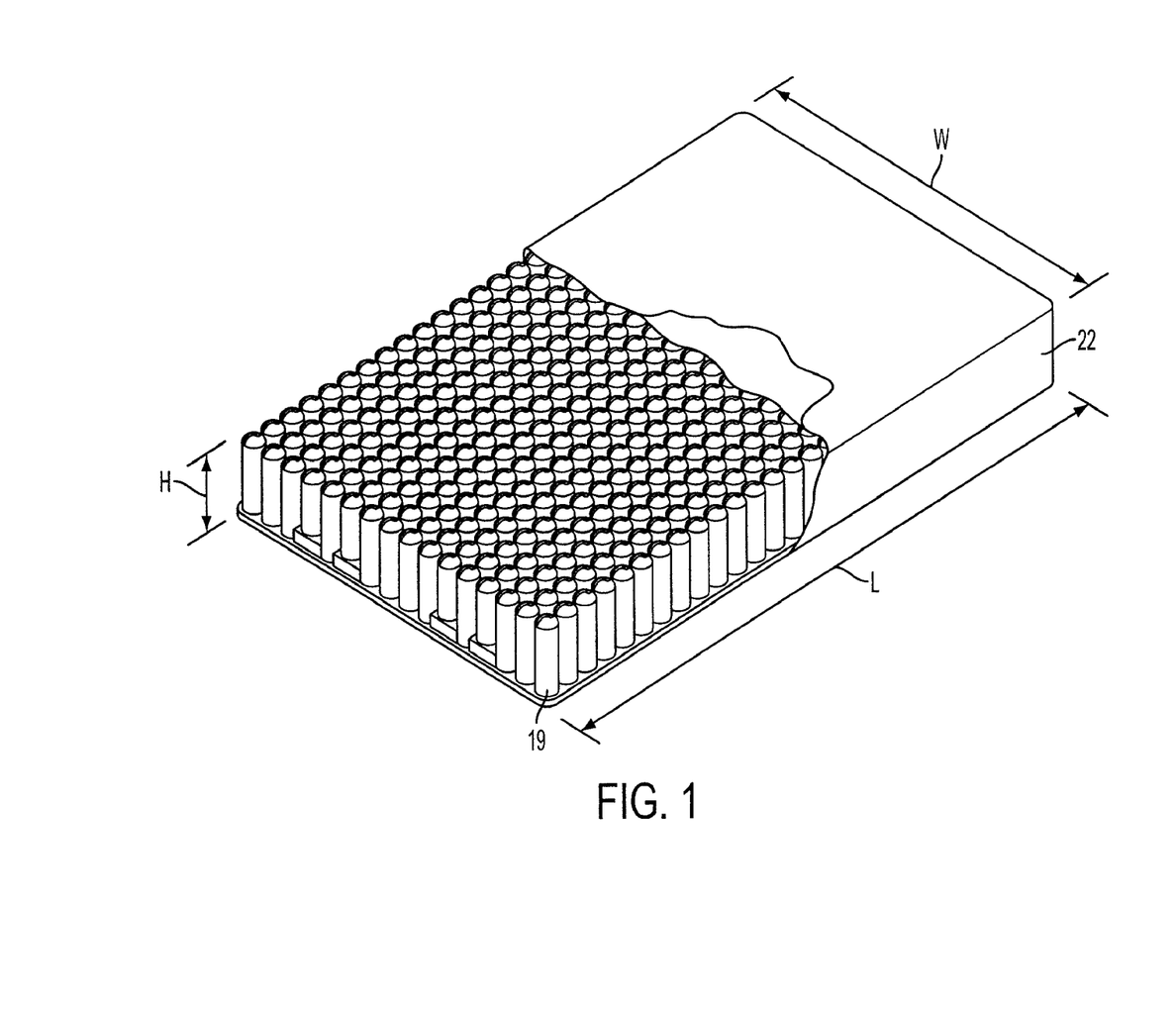
FIG. 1 illustrates a conventional pocketed coil spring mattress that has multiple rows of pocketed coil springs that extend transversely.

FIG. 1 illustrates a conventional pocketed coil spring mattress 22 that has multiple rows of pocketed coil springs 19 that extend transversely. The conventional pocketed coil spring mattress 22 in FIG. 1 is shown having a width "W," a length "L," and a height "H."

Figure 2:
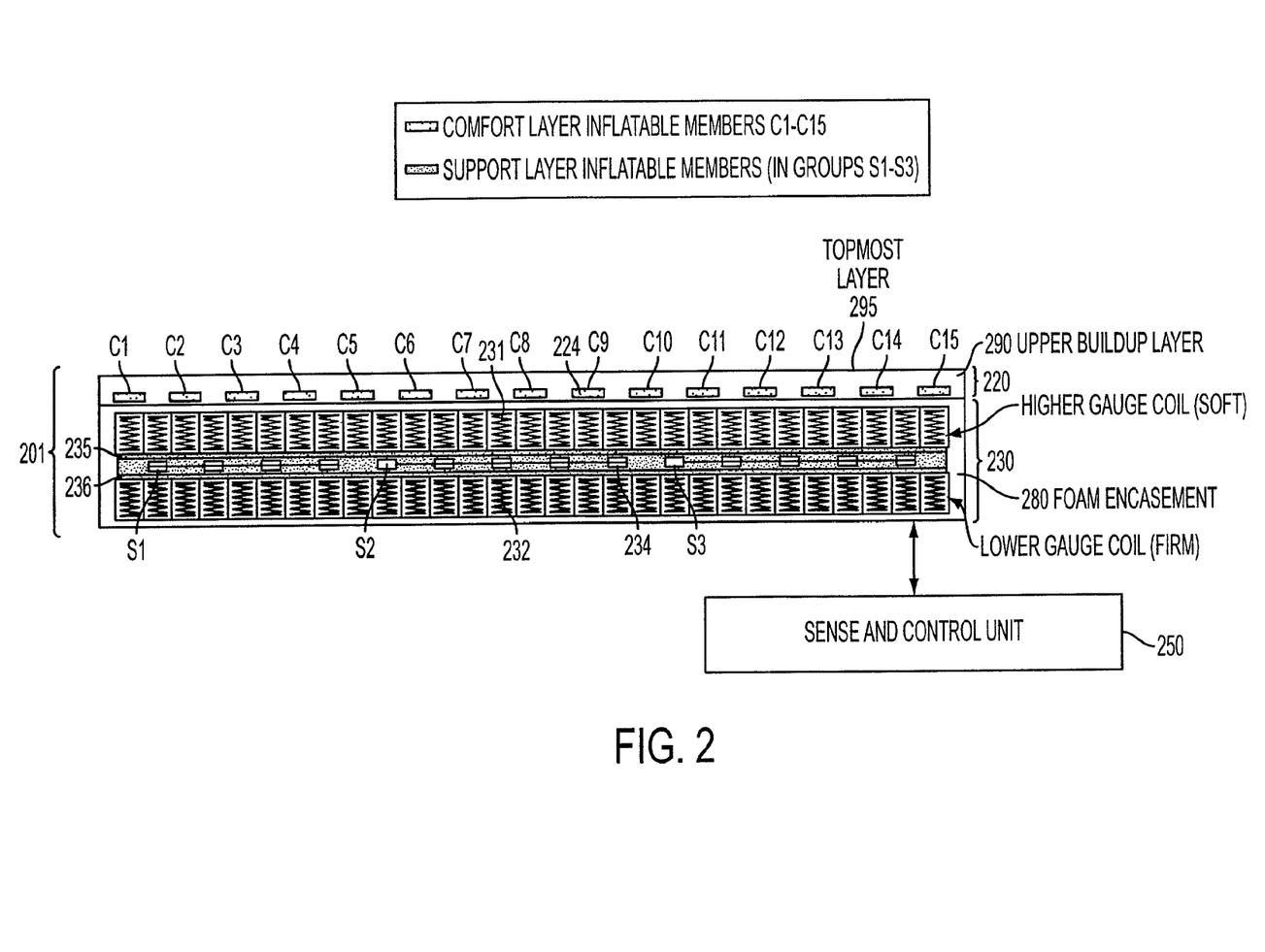
FIG. 2 illustrates a cross-sectional view of a sleep system employing a variable support and comfort control system according to an illustrative embodiment of the present invention.

In contrast to the conventional mattress shown in FIG. 1, FIG. 2 illustrates a cross-sectional view of a mattress employing a variable support and variable comfort control system according to an illustrative embodiment of the present invention. As shown in FIG. 2, a variable support and variable comfort sleep system 201 comprises a variable comfort layer 220 and a variable support layer 230 that is disposed below the variable comfort layer 220. The variable comfort layer 220 further comprises an upper buildup layer 290 and a topmost layer 295. Further, as shown in FIG. 2, the variable sleep system 201 is connected to a sense and control unit 250.

According to an illustrative embodiment of the present invention, the variable comfort layer 220 and the variable support layer 230 are configured to allow adjustment to (among other things) the two primary components of sleep systems discussed above that affect a person's overall sleep experience, namely, comfort and support. That is, the embodiment shown in FIG. 2 operates to adjust the support characteristics of the variable sleep system 201 and to adjust the comfort characteristics of the variable sleep system 201.

As explained in greater detail below, the variable comfort layer 220 is configured to allow adjustment to the pressure applied to a top region of the variable sleep system 201 at various regions of a person's body. More particularly, variable comfort layer 220 is configured to allow immediate adjustments to the region of a sleep system that typically delivers comfort to a person's body through the use of comfort layers at a top region of the sleep surface.

On the other hand, the variable support layer 230 is configured to allow adjustment to the pressure applied to a region of the variable sleep system 201, located below the variable comfort layer 220, at various regions of the person's body. More particularly, the variable support layer 230 is configured to allow immediate adjustments to the region of a sleep system that typically delivers support to a person's body through the resistance provided by the innersprings.

As explained in detail below, by adjusting both the variable comfort layer 220 and the variable support layer 230, it is possible to adjust the variable sleep system 201 so that it provides the best possible combination of comfort and support to the person. Adjustments to the variable support layer 230 may be performed automatically based on body variances of the person, or manually based on the person's comfort preferences.

FIG. 2 shows an illustrative embodiment wherein the variable support layer 230 comprises a layer of upper coils 231 and a layer of lower coils 232. As shown in FIG. 2, the layer of upper coils 231 and the layer of lower coils 232 are enclosed by a foam encasement 280. According to the illustrative embodiment shown in FIG. 2, the layer of upper coils 231 and the layer of lower coils 232 are arranged in rows of coils that extend in a longitudinal direction of the variable sleep system 201 (i.e., the rows of coils extend from the head of the variable sleep system 201 to the foot of the variable sleep system 201). However, the present invention is not limited to this illustrative configuration of coils and the rows of coils comprising the layer of upper coils 231 and the layer of lower coils 232 may extend laterally across the width of the variable sleep system 201 consistent with the present invention. More generally, the rows of coils comprising the layer of upper coils 231 and the layer of lower coils 232 may comprise any arrangement of coils and the present invention is not limited to any specific configuration of coils.

Further, according to one illustrative embodiment, the coils comprising the layer of upper coils 231 and the layer of lower coils 232 comprise what is known in the industry as pocketed coil springs, in which each spring is individually enclosed within a pocket of material. However, the present invention is not limited to a configuration employing pocketed coils and a wide variety of support devices can be used consistent with the present invention, including, but not limited to, layers of plastic based materials or other engineered support systems.

According to the illustrative embodiment shown in FIG. 2, the coils comprising the layer of upper coils 231 are formed of a higher gauge material than the coils comprising the layer of lower coils 232. For example, the coils comprising the layer of upper coils 231 may be formed of 16 gauge wire (i.e., softer coils), whereas the coils comprising the layer of lower coils 232 may be formed of 14 gauge wire (i.e., firmer coils). As such, when force is applied to the top of the variable sleep system 201 (e.g., when a person lies down on the variable sleep system 201), the coils comprising the layer of upper coils 231 compress more easily than the coils comprising the layer of lower coils 232.

A plurality of support layer inflatable members or bladders 234 are disposed between the layer of upper coils 231 and the layer of lower coils 232. As shown in FIG. 2, there are three groups of support layer inflatable members 234, which are respectively referenced as S1, S2 and S3. However, the present invention is not limited to the configuration shown in FIG. 2 and any number of groups of support layer inflatable members 234 may be employed. According to the illustrative embodiment shown in FIG. 2, the support layer inflatable members 234 are pneumatic and are connected to an optional pump/vacuum unit 310 (shown in FIG. 3) via pneumatic tubes. However, the present invention is not limited to this illustrative configuration and other gasses or fluids may be employed to inflate/deflate the support layer inflatable members 234 to a desired pressure. In particular, the pump/vacuum unit 310 is an optional component that is not a requisite aspect of the present invention.

The support layer inflatable members 234 may be constructed of a variety of materials including, but not limited to plastic, vinyl, neoprene, rubber and the like. According to the illustrative embodiment shown in FIG. 2, the support layer inflatable members 234 extend in a lateral direction across the width of the variable sleep system 201.

Figure 5:
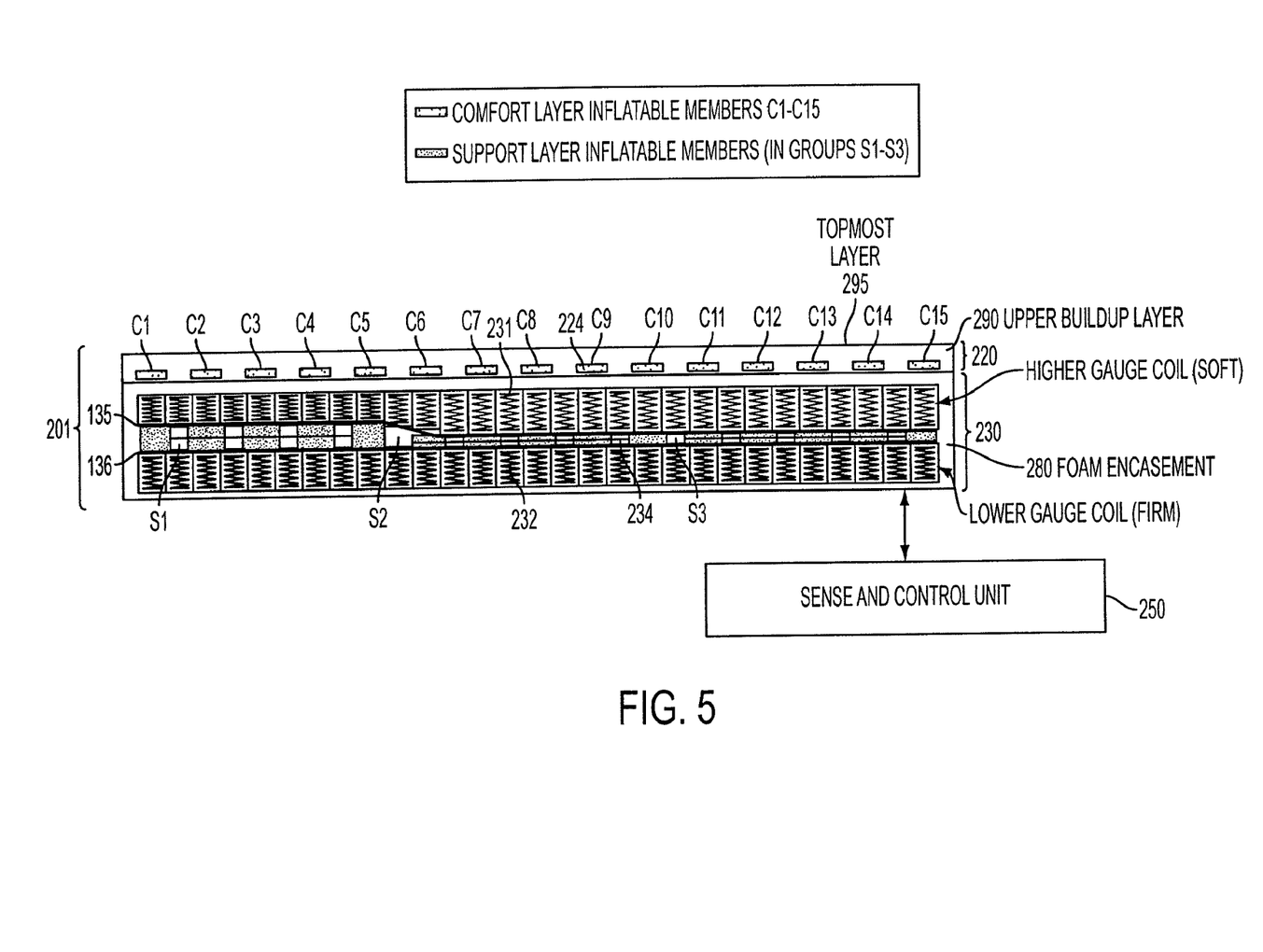
FIG. 5 illustrates a cross-sectional view of a sleep system employing a variable support and comfort control system wherein a group S1 of support layer inflatable members are inflated according to an illustrative embodiment of the present invention.

As shown in FIGS. 2 and 5, the support layer inflatable members 234 are configured such that, when inflated, the support layer inflatable members 234 apply forces to the layer of upper coils 231 and to the layer of lower coils 232. FIG. 2 illustrates a cross-sectional view of the variable sleep system 201 wherein a group S1 of support layer inflatable members 234 are deflated. On the other hand, FIG. 5 illustrates a cross-sectional view of the variable sleep system 201 wherein the group of inflatable members S1 is inflated.

Accordingly, by controlling the inflation/deflation of the support layer inflatable members 234, the support characteristics of the variable sleep system 201 can be adjusted. For example, if the sense and control unit 250 automatically determines, based on the person's body variances, to provide more support for the person's lower back, or receives a manual instruction to do so, then the support layer inflatable members 234 disposed in a region corresponding to the person's lower back can be controlled to further inflate. Consequently, the support layer inflatable members 234 would apply greater forces to certain coils within the layer of upper coils 231 and the layer of lower coils 232 that are disposed in a region corresponding to the person's lower back, causing the aforementioned coils to further compress and, in turn, apply greater support to the person's lower back.

Figure 3:
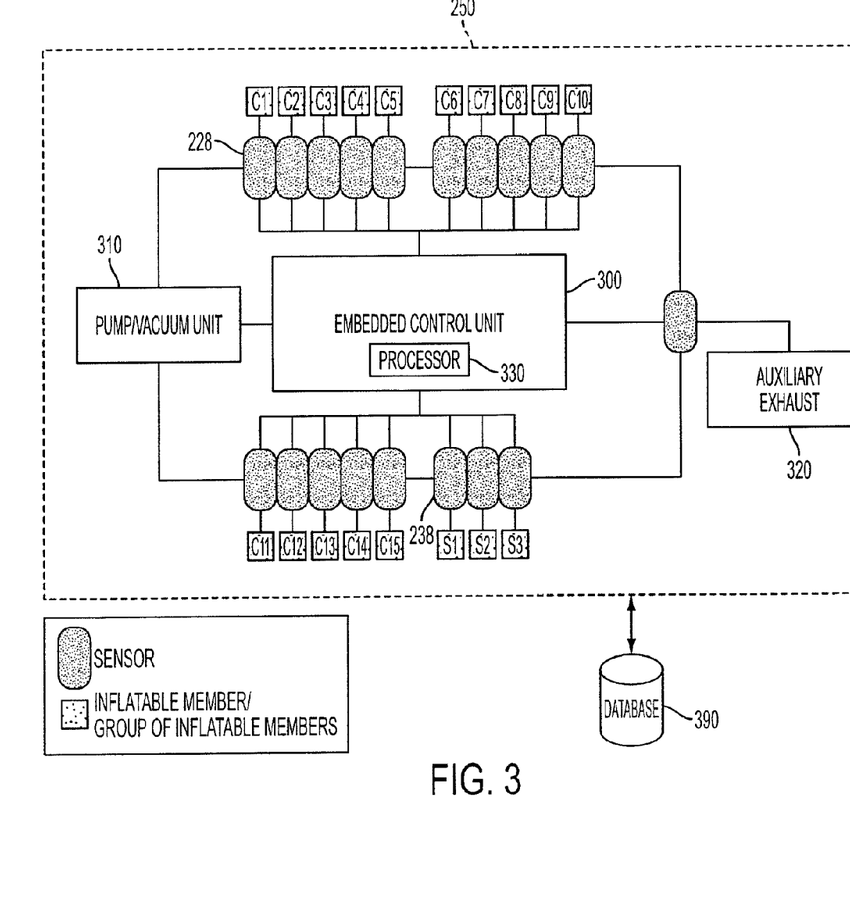
FIG. 3 illustrates a sense and control unit according to an illustrative embodiment of the present invention.

As shown in FIG. 2, the variable sleep system 201 is connected to a sense and control unit 250. A detailed illustration of an illustrative sense and control unit 250 is shown in FIG. 3. As shown in FIG. 3, the sense and control unit 250 comprises a plurality of comfort layer sensors 228, which are respectively associated with the comfort layer inflatable members 224, which are respectively referenced as C1, C2, C3, C4, C5, C6, C7, C8, C9, C10, C11, C12, C13, C14 and C15. The sense and control unit 250 further comprises a plurality of support layer sensors 238, which are respectively associated with the groups S1, S2 and S3 of support layer inflatable members 234.

As further illustrated in FIG. 3, the sense and control unit 250 comprises an embedded control unit 300, a pump/vacuum unit 310 and an auxiliary exhaust unit 320. The embedded control unit further comprises a processor 330. The pump/vacuum unit 310 may be controlled by the embedded control unit 300 to pump or suck air as desired. The auxiliary exhaust unit 320 actively or passively exhausts gas or fluid from the support layer inflatable members 234 and the comfort layer inflatable members 224. According to the illustrative embodiment shown in FIG. 3, the sense and control unit 250 is connected to a database 390.

As shown in FIG. 3, each of the plurality of support layer sensors 238 are connected to a respective group of the support layer inflatable members 234. For example, a group of five support layer inflatable members 234 on the left region of the variable sleep system 201, as shown in FIG. 2, is connected to the support layer sensor S1. Likewise, a group of five support layer inflatable members 234 in the center region of the variable sleep system 201, as shown in FIG. 2, is connected to the support layer sensor S2. Further, a group of five support layer inflatable members 234 on the right side of the variable sleep system 201, as shown in FIG. 2, is connected to the support layer sensor S3. However, the present invention is not limited to the specific configuration shown in FIGS. 2 and 3 and a wide variety of groupings of the support layer sensors 238 may be used consistent with the present invention. Moreover, each of the plurality of support layer sensors 238 can be connected to a respective one of the support layer inflatable members 234.

Each of the support layer sensors 238 is configured to provide real time measurements relating to the pressure of a respective support layer inflatable member 234 or a respective group of support layer inflatable members 234. As such, when a person is positioned on the variable sleep system 201, measurements relating to the pressure of respective support layer inflatable members 234 can be acquired and analyzed. Using such measurements, a support layer pressure profile of the person can be obtained and used to determine adjustments that would provide the most suitable sleep system support layer characteristics for the person.

According to the illustrative embodiment shown in FIG. 2, the variable support layer 230 comprises fifteen support layer inflatable members 234, but the present invention is not limited to this configuration and a larger or smaller number of support layer inflatable members 234 may be employed consistent with the present invention.

According to the illustrative embodiment illustrated in FIG. 2, each support layer inflatable member 234 is configured to apply forces to a plurality of rows of upper coils 231 and to a plurality of rows of lower coils 232. That is, each support layer inflatable member 234 is aligned with more than one row of coils. Alternatively, each support layer inflatable member 234 can be positioned without regard to the position of the individual coils of the layer of upper coils 231 and the layer of lower coils 232. In one embodiment, the support layer inflatable members 234 may be attached to the coils of the layer of upper coils 231 and to the layer of lower coils 232, for example, by gluing each support layer inflatable member 234 to the coils.

Moreover, a first force dispersing cover 235 may be disposed between the support layer inflatable members 234 and the coils of the layer of upper coils 231. Among other things, the first force dispersing cover 235 facilitates the dispersion of the force applied by each support layer inflatable member 234 among a plurality of rows of upper coils 231. The first force dispersing cover 235 may be comprised of a wide variety of materials including, but not limited to, non-woven fabric, polystyrene, etc.

Likewise, a second force dispersing cover 236 may be disposed between the support layer inflatable members 234 and the layer of lower coils 232. Among other things, the second force dispersing cover 236 facilitates the dispersion of the force applied by each support layer inflatable member 234 among a plurality of rows of lower coils 232.

According to one illustrative embodiment, the first force dispersing cover 235 may be glued to the coils of the layer of upper coils 231 and the second force dispersing cover 236 may be glued to the layer of lower coils 232. By inserting the first and second force dispersing covers 235 and 236 between the coils and the inflatable members, the force applied by expanding each respective inflatable member is spread over a greater area and hence across a greater number of coils. In this illustrative configuration, the first and second force dispersing covers 235 and 236 disperse the force of the inflatable members to achieve a greater effect on the coils over a greater area.

As shown in FIG. 2, an upper buildup layer 290 is disposed above the layer of upper coils 231. The upper buildup layer 290 comprises a plurality of comfort layer inflatable members 224 that are disposed above the layer of upper coils 231 and below a topmost layer 295. The configuration of each of the respective comfort layer inflatable members 224 is similar to the configuration of the support layer inflatable members 234, discussed above.

Consistent with the illustrative embodiment depicted in FIG. 2, the comfort layer inflatable members 224 are configured such that, when inflated, the comfort layer inflatable members 224 apply forces to the layer of upper coils 231, to the upper buildup layer 290 and to the topmost layer 295. Accordingly, by controlling the inflation/deflation of the comfort layer inflatable members 224, the comfort characteristics of the variable sleep system 201 (among other things) can be adjusted. For instance, the inflation/deflation of the comfort layer inflatable members 224 can be controlled to change the comfort level of the variable sleep system 201 by making the variable comfort layer 220 either firmer or softer. That is, inflating or deflating a respective one of the comfort layer inflatable members 224 has the effect of compressing or decompressing upper buildup layer 290 and thereby creating a different interface profile (or feel) for the occupant of the variable sleep system 201.

Thus, if the sense and control unit 250 automatically determines, based on the person's body variances, to make the variable comfort layer 220 firmer under the shoulder region of the person, or receives a manual instruction to do so, then the respective comfort layer inflatable member(s) 224 under the person's shoulder region is/are further inflated. On the other hand, if the sense and control unit 250 automatically determines to make the variable comfort layer 220 softer under the shoulder region of the person, or receives a manual instruction to do so, then the respective comfort layer inflatable member(s) 224 under the person's shoulder region is/are further deflated so as to provide more cushion in those areas.

Additionally, as shown in FIGS. 2 and 3, each of a plurality of comfort layer sensors 228 are connected to a respective one of the comfort layer inflatable members 224. Each of the comfort layer sensors 228 is configured to provide real time measurements relating to the pressure of a respective comfort layer inflatable member 224. According to the illustrative embodiment shown in FIGS. 2 and 3, fifteen comfort layer inflatable members 224 are connected to fifteen comfort layer sensors 228. However, the present invention is not limited to this configuration and a larger or smaller number of comfort layer sensors 228 may be employed consistent with the present invention.

Moreover, as shown in FIG. 2, each of the comfort layer inflatable members 224 is aligned with a respective one of the support layer inflatable members 234, however, such alignment is not necessary and illustrative embodiments of the invention my comprise configurations of comfort layer inflatable member 224 and support layer inflatable members 234 that are not aligned.

Also, according to the illustrative embodiment shown in FIG. 2, the comfort layer inflatable members 224 need not be aligned with a respective row of the upper coils 231. Indeed, a respective comfort layer inflatable member 224 may be aligned with more than one of the rows of upper coils 231. Alternatively, the comfort layer inflatable members 224 can be positioned without regard to the position of the individual upper coils 231.

Importantly, when a person is positioned on the variable sleep system 201, measurements relating to the pressure of respective comfort layer inflatable members 224 can be acquired and analyzed. Using such measurements, a comfort layer pressure profile of the person can be obtained and used to determine adjustments that would provide the most suitable sleep system comfort layer characteristics for the person.

Although the illustrative embodiment shown in FIG. 2 comprises a variable comfort layer 220 and a variable support layer 230, the present invention is not limited to this configuration. In fact, illustrative embodiments of the present invention may include only the variable comfort layer 220, or only the variable support layer 230.

Figure 6A:
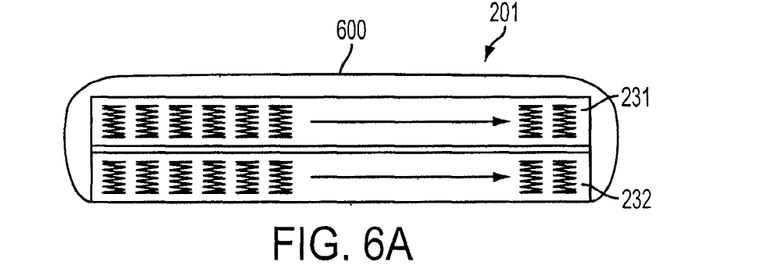
FIG. 6A illustrates a cross-sectional view of a sleep system employing a variable support and comfort control system having a third force dispersing cover according to an illustrative embodiment of the present invention.
Figure 6B:
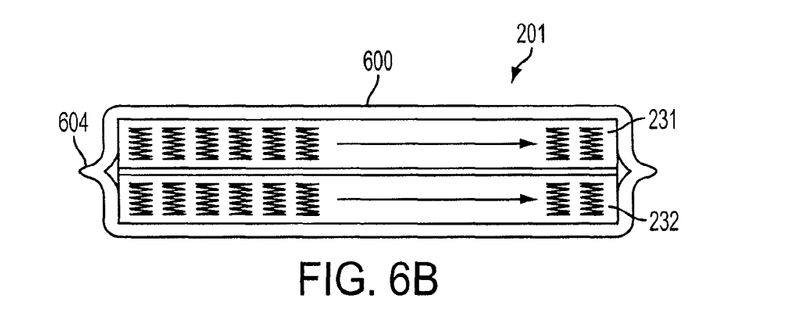
FIG. 6B illustrates a cross-sectional view of a sleep system employing a variable support and comfort control system having a third force dispersing cover according to an illustrative embodiment of the present invention.

Additionally, according to illustrative embodiments of the present invention, as shown in FIGS. 6A and 6B, the variable sleep system 201 may comprise a third force dispersing cover 600, which is wrapped around the layer of upper coils 231 and the layer of lower coils 232. According to the illustrative embodiment shown in FIGS. 6A and 6B, the third force dispersing cover 600 extends the length of the variable sleep system 201, but does not extend over the head or the foot of the variable sleep system 201. As shown in FIGS. 6A and 6B, the third force dispersing cover 600 is, for illustrative purposes, shown as loosely surrounding the layer of upper coils 231 and the layer of lower coils 232. However, illustrative embodiments of the present invention may comprise a third force dispersing cover 600 that is tightly wrapped around the layer of upper coils 231 and the layer of lower coils 232. Among other things, the third force dispersing cover 600 disperses the forces applied by the upper coils 231 and the layer of lower coils 232 over a greater area of the foam encasement layer 280 (shown in FIGS. 2 and 5) and, thus, helps to prevent a crowning effect that may occur at the top surface of the variable sleep system 201.

According to the illustrative embodiment shown in FIG. 6A, the third force dispersing cover 600 is attached to a bottom border of the variable sleep system 201 (e.g., border wire) and does not extend below the layer of lower coils 232.

Alternatively, according to the illustrative embodiment shown in FIG. 6B, the third force dispersing cover 600 extends below the layer of lower coils 232. Further, as shown in FIG. 6B, two opposing portions of the third force dispersing cover 600 are attached together at attachment portion 604. For example, the two opposing portions of the third force dispersing cover 600 may be attached via an ultrasonic weld, sewing, staples, etc. However, the present invention is not limited to the two exemplary configurations shown in FIGS. 6A and 6B and the third force dispersing cover 600 may assume a wide variety of configurations.

According to an illustrative embodiment, the variable comfort layer 220 may be configured to comprise a plurality of different zones, each zone providing respective comfort characteristics. For instance, the variable comfort layer 220 may comprise seven different comfort zones, wherein each comfort zone comprises at least one comfort layer inflatable member 224 and wherein the seven different comfort zones are not equal in size. On the other hand, the variable support layer 230 may comprise three different support zones, wherein each support zone comprises at least one support layer inflatable member 234, wherein the three different support zones are not equal in size.

Consistent with the present invention, the support layer sensors 238 and the comfort layer sensors 228 provide the ability to measure a wide variety of data. For example, when a person is positioned on the variable sleep system 201, data provided by the support layer sensors 238 and the comfort layer sensors 228 can be analyzed to determine, among other things, the person's weight, weight distribution, body position, breathing rate, heart rate, state of sleep, etc. Further, such data can be acquired and analyzed over time to determine a variety of body variances of the person while the person sleeps.

As shown in FIGS. 2 and 3, the support layer inflatable members 234, the support layer sensors 238, the comfort layer inflatable members 224, and the comfort layer sensors 228 are all connected to the sense and control unit 250. By using the information collected by the sense and control unit 250, the general body dimensions and weight distribution (among other things) of a person disposed on the variable sleep system 201 can be statistically predicted. The processor 330 can use these statistically predicted values to determine adjustments to the combinations of zoned support and zoned comfort provided by the variable sleep system 201 that are needed to produce a healthy sleep system. More generally, the processor 330 can measure and analyze the effect of the person's body on various points on the variable comfort layer 220 and the variable support layer 230 and can record this measurement data over time.

Thus, according to one illustrative embodiment, a person positions themselves on the variable sleep system 201 and the processor 330 measures and analyzes the effect of the person's body on various points on the variable comfort layer 220 and the variable support layer 230. Using such measurement data, the processor 330 then determines the optimal adjustments to the support layer inflatable members 234 and comfort layer inflatable members 224 that would provide the person with the best combination of zoned support and zoned comfort. The sense and control unit 250 then adjusts the support layer inflatable members 234 and comfort layer inflatable members 224 to their respective determined optimal levels, thus providing the variable sleep system 201 with optimal support and comfort characteristics.

Further, according to another illustrative embodiment, the processor 330 records measurement data regarding the effect of the person's body on various points on the variable comfort layer 220 and the variable support layer 230 over time. By analyzing such data, the processor 330 can detect a wide variety of body variances of the person and can determine optimal adjustments to the support layer inflatable members 234 and comfort layer inflatable members 224 based on such detected variances.

According to one illustrative embodiment, the sense and control unit 250 can detect and provide immediate automatic adjustments to the comfort layer inflatable members 224 and the support layer inflatable members 234 based on measurements taken about the person during sleep, as to continuously provide the variable sleep system 201 with custom-determined optimal comfort and support characteristics, respectively. In particular, during the course of a night, the sense and control unit 250 can detect and analyze a wide variety of body variances that a person experiences including, but not limited to, a person's weight distribution, body position, breathing rate, heart rate, state of sleep, sleep quality etc. Thus, the sense and control unit 250 can automatically adjust both the comfort layer inflatable members 224 and the support layer inflatable members 234 in immediate response to such body variances so as to continuously provide optimal support and comfort characteristics to the person throughout the night.

For example, if based on measurements regarding changes in the person's sleep quality, the sense and control unit 250 determines that additional support is needed in a particular zone of the variable sleep system 201 to improve sleep quality, then the support layer inflatable members 234 in that zone can be adjusted.

Or, for instance, the sense and control unit 250 can determine that a person has rolled over in their sleep to a new sleeping position (e.g., the person has rolled from their back to their side) and that, as a result, additional support is needed in the person's hip area. Accordingly, the sense and control unit 250 can then adjust designated support layer inflatable member(s) 234 corresponding to the region of the person's hip area by increasing the pressure within those designated support layer inflatable member(s) 234. Consequently, the designated support layer inflatable member(s) 234 would expand, causing the coil(s) of the layer of upper coils 231 located above the designated support layer inflatable member(s) 234 to compress. This, in effect, causes the coil(s) corresponding to the region of the person's hip area to be biased by the inflation of the designated support layer inflatable member(s) 234. Accordingly, additional support would be provided in that area of the variable sleep system 201 that corresponds to the person's hip area.

In addition to providing immediate automatic adjustments like those examples discussed above, the sense and control unit 250 can also measure and analyze a person's body variances (e.g., gains or losses in weight, changes in weight distribution, etc.) and sleeping habits over an extended period of time. Hence, the sense and control unit 250 can adjust the comfort layer inflatable members 224 and the support layer inflatable members 234 in response to such long-term variances so as to continuously provide optimal support and comfort characteristics to the person over an extended period.

By way of illustration, suppose a person gradually gains substantial weight during the years subsequent to their purchase of the sleep system 201. In such a case, the sense and control unit 250 would detect, measure and analyze this gradual variance in weight over time. Based on such an analysis, the sense and control unit 250 might, for example, then determine that additional support is required, throughout the entire support layer 230, to compensate for the person's weight gain and to thereby provide the variable sleep system 201 with the optimal support characteristics for the person. Accordingly, as the person gains weight over time, the sense and control unit 250 would automatically control each of the support layer inflatable members 234 to further inflate, as necessary, to provide the optimal support characteristics for the person corresponding to their gradual variance in weight.

Consistent with the present invention, the optimal pressure levels for each of the respective comfort layer inflatable members 224 and support layer inflatable members 234 and at which the variable sleep system 201 provides optimal comfort and support characteristics to the person can be determined in a number of ways. For example, such optimal pressure levels can be determined by analyzing data obtained by observing a plurality of different persons of varying physical attributes (e.g., persons of different heights, weights, weight distributions, waist widths, shoulder widths, etc.) as they are positioned on a variety of different sleep systems having different comfort and support characteristics, in a variety of different sleeping positions and by recording observed data in the database 390. By recording such observed data in the database 390, along with which particular comfort and support characteristics provide each respective person with the best support (e.g., spinal alignment, etc.) and comfort characteristics (e.g., lowest amount of interface pressure, etc.) a correspondence between particular physical attributes of persons and suitable comfort and support characteristics can be established and stored in the database 390.

Examples of apparatuses and methods for objectively evaluating a person on a sleep system so as to determine the optimal comfort and support characteristics for the person have been developed by the inventors of the present application, as set forth in the aforementioned related Provisional Application. However, such apparatuses and examples are merely examples and the present invention is not limited to these examples.

According to one illustrative embodiment, the optimal pressure levels of the support layer inflatable members 234 and comfort layer inflatable members 224 for a person can be calculated as set forth in the aforementioned related Provisional Application using the test bed disclosed therein. Such calculations can then be used to provide the most suitable variable support and variable comfort settings to which the variable sleep system 201 can be adjusted. For example, the calculations from the aforementioned test bed can be provided to and stored in the database 390 in a variety of ways including, but not limited to, transfer via wireless or wired communication, transfer via storage media, manual data input, etc.

That is, by way of illustration, a prospective sleep system purchaser could visit a sleep system showroom where an evaluation of the person on a sleep system can be performed according to the aforementioned related Provisional Application. As a result of this evaluation, the prospective sleep system purchaser would be provided with optimal variable support and variable comfort settings to be transferred to a variable sleep system 201 in the purchaser's home. Thus, the variable sleep system 201 would adjust the support layer inflatable members 234 and comfort layer inflatable members 224 to the optimal pressure levels so as to provide the optimal support and comfort characteristics to the purchaser.

According to an illustrative embodiment of the present invention, a person can manually input body data to the sense and control unit 250, including, but not limited to, data such as the person's height, weight, body size, etc. Using such manually inputted body data, the processor 330 then determines the optimal adjustments to the support layer inflatable members 234 and comfort layer inflatable members 224 that would provide the person with the best combination of zoned support and zoned comfort. The sense and control unit 250 then adjusts the support layer inflatable members 234 and comfort layer inflatable members 224 to their respective determined optimal levels, thus providing the variable sleep system 201 with optimal support and comfort characteristics using the manually inputted body data.

In addition to the support and comfort characteristics of the variable sleep system 201 being automatically adjustable, as described above, a person could also manually control the support and comfort characteristics of the variable sleep system 201 based on support and comfort levels that the person selects. For example, if a person desired to make the variable sleep system 201 feel firmer under the person's shoulders, then the person could control the comfort layer inflatable member(s) 224 corresponding to the person's shoulder region to be further inflated by increasing the pressure of the respective comfort layer inflatable member(s) 224. When the respective comfort layer inflatable member(s) 224 corresponding to the person's shoulder region inflate and expand, the respective comfort layer inflatable member(s) 224 cause the coils of the layer of upper coils 231 below to compress and cause the region of the upper buildup layer 290 above to compress. Consequently, the variable sleep system 201 would apply greater contact pressure to the region corresponding to the person's shoulders (i.e., this region would feel firmer).

Conversely, if the person desired to make the variable sleep system 201 feel softer, then the person could control the sense and control unit 250 to reduce the pressure of certain comfort layer inflatable member(s) 224 (e.g., by releasing air from certain comfort layer inflatable member(s) 224) so as to cause the variable sleep system 201 to apply less contact pressure to the person in those areas (i.e. those areas would feel softer and have more cushion).

Although the above example describes manual adjustments to the comfort characteristics of the variable sleep system 201, a person can also manually adjust the support characteristics of the variable sleep system 201 in an analogous manner. Indeed, in contrast to conventional devices like the mattress described in the '182 patent (which only provides an overall increase in support of less 15%), indentation load deflection tests show that illustrative embodiments of the present invention exhibit an overall increase in support of more than 100%.

Furthermore, although the illustrative embodiments described above relate to varying the support and comfort characteristics of the variable sleep system 201 to provide the optimal support and comfort for a single person, the present invention can also be employed to vary the support and comfort characteristics of the variable sleep system 201 to provide the optimal support and comfort for a person and their sleeping partner. According to one illustrative embodiment, the variable sleep system 201 may comprise two separate variable surfaces so that optimal support and comfort characteristics can be provided to two persons at the same time, even if the two persons have significantly different physical attributes. Thus, apparatuses and methods consistent with the present invention also provide automatic adjustment of the support and comfort characteristics of a sleep system comprising two variable surfaces in response to body variances of two persons, respectively. Further, aspects of the present invention provide manual adjustment of the support and comfort characteristics of a sleep system comprising two variable surfaces based on support and comfort levels that two persons select, respectively.

Figure 4:
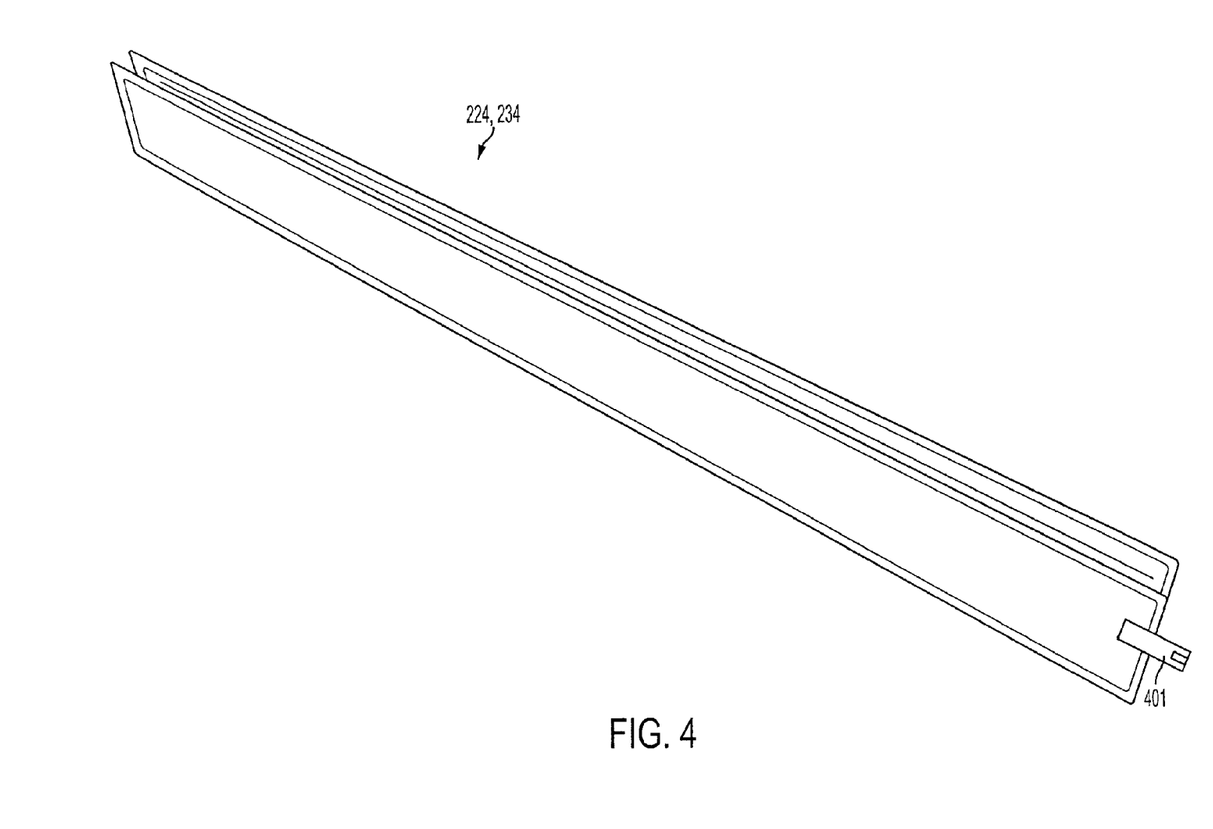
FIG. 4 illustrates a view of an inflatable member according to an illustrative embodiment of the present invention.

FIG. 4 illustrates a view of an inflatable member 224 or 234 according to an illustrative embodiment of the present invention. Although one illustrative shape and configuration of the inflatable member is shown in FIG. 4, the inflatable members 224 and 234 may assume other shapes and configurations consistent with the present invention. Further, the comfort layer inflatable members 224 may assume shapes and/or configurations that are different from the shapes and/or configurations of the support layer inflatable members 234. As shown in FIG. 4, each of the inflatable members comprises a valve 401.

Figure 7A:
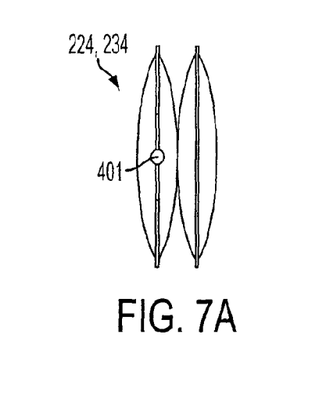
FIG. 7A illustrates a side view of one end of an inflatable member according to an illustrative embodiment of the present invention.
Figure 7B:
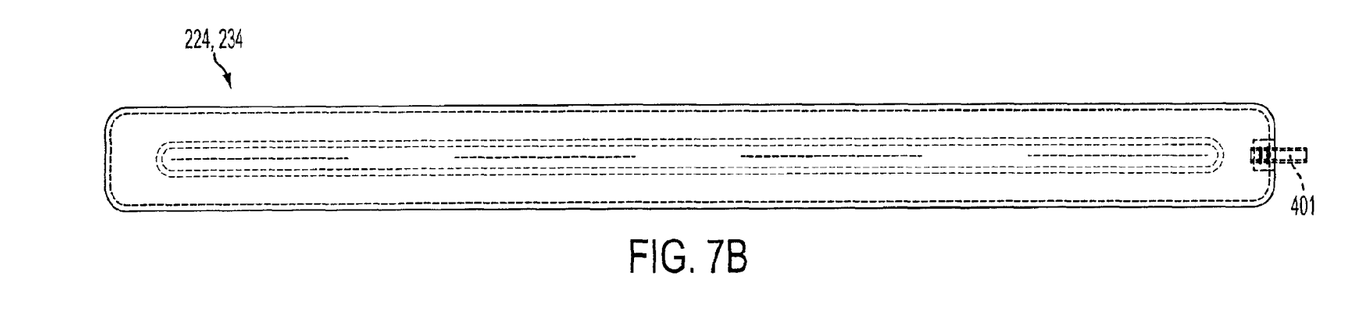
FIG. 7B illustrates a top view of an inflatable member according to an illustrative embodiment of the present invention.

FIG. 7A illustrates a side view of one end of an inflatable member 224 or 234 according to an illustrative embodiment of the present invention. FIG. 7B illustrates a top view of an inflatable member 224 or 234 according to an illustrative embodiment of the present invention.

The method of controlling the support and comfort of a mattress according to an illustrative embodiment of the invention can also be embodied as computer readable codes on a computer readable recording medium. The computer readable recording medium can be any data storage device that can store data which can be read by a computer or a computer system. Examples of the computer readable recording medium include, but are not limited to, read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion.

While the present invention has been particularly shown and described with reference to illustrative embodiments thereof, it will be understood by those of ordinary skill in the art that various changes in form and details may be made therein without departing from the spirit and scope of the invention as defined by the appended claims. The illustrative embodiments should be considered in a descriptive sense only and not for purposes of limitation. Therefore, the scope of the invention is defined not by the detailed description of the invention but by the claims set forth in the related non-provisional application and all differences within the scope will be construed as being included in the present invention.

What is claimed is:

1. A sleep system comprising:
 a sleep support member comprising:
  a comfort layer comprising:
   a plurality of comfort layer inflatable members; and
   a comfort layer sensor configured to provide data relating to respective pressures of the comfort layer inflatable members;
  a data analysis unit configured to analyze data provided by the comfort layer sensor and to generate analyzed comfort layer data; and
  a control unit configured to control a pressure within at least one of the comfort layer inflatable members using the analyzed comfort layer data,
  wherein the data analysis unit is configured to determine an adjustment to a pressure of at least one of the comfort layer inflatable members that would cause the sleep support member to provide a more suitable combination of comfort characteristics and support characteristics for a person disposed on the sleep support member,
  wherein the control unit is configured to adjust the pressure of the at least one of the comfort layer inflatable members based on the determined adjustment, and
  wherein the sleep support member further comprises a support layer.

2. The sleep system according to claim 1, wherein the comfort layer inflatable members are configured such that the pressure within each of the respective comfort layer inflatable members can be controlled using a fluid.

3. The sleep system according to claim 1, wherein the data analysis unit is configured to analyze data provided by the comfort layer sensor relating to body variances of the person.

4. The sleep system according to claim 1,
 wherein the support layer comprises:
  a plurality of support layer inflatable members; and
  a support layer sensor configured to provide data relating to respective pressures of the support layer inflatable members;
 wherein the data analysis unit is configured to analyze data provided by the support layer sensor and to generate analyzed support layer data; and
 wherein the control unit is configured to control a pressure of at least one of the support layer inflatable members using the analyzed support layer data.

5. The sleep system according to claim 4, wherein the support layer is disposed below the comfort layer.

6. The sleep system according to claim 4, wherein the support layer comprises:
 a layer of upper coils; and
 a layer of lower coils,
 wherein the support layer inflatable members are disposed below the layer of upper coils and above the layer of lower coils.

7. The sleep system according to claim 4, wherein the support layer comprises a layer of coils, and
 wherein the support layer inflatable members are disposed above the layer of coils.

8. The sleep system according to claim 1, wherein the data analysis unit is configured to analyze the data provided by the comfort layer sensor to determine at least one of the person's weight, the person's weight distribution, the person's breathing rate, the person's heart rate and the person's state of sleep.

9. The sleep system according to claim 1, wherein the comfort characteristics comprise interface pressure between the person and the sleep support member.

10. The sleep system according to claim 1, wherein the support characteristics comprise spinal alignment for the person.

11. The sleep system according to claim 1, wherein the data relating to respective pressures of the comfort layer inflatable members is data measuring respective pressures inside the comfort layer inflatable members.

12. The sleep system according to claim 1, wherein the support layer is disposed below the comfort layer.

13. A method of controlling a variable sleep support member, the method comprising:
 determining whether a person is disposed on the sleep support member;
 if a person is disposed on the sleep support member, then:
  analyzing data relating to respective pressures of a plurality of comfort layer inflatable members that are arranged in a comfort layer of the sleep support member to generate analyzed comfort layer data;
  determining an adjustment to a pressure of at least one of the comfort layer inflatable members that would cause the sleep support member to provide a more suitable combination of comfort characteristics and support characteristics for the person; and
  controlling the determined adjustment to the pressure of the at least one of the comfort layer inflatable members using the analyzed comfort layer data,
 wherein the sleep support member further comprises a support layer.

14. The method according to claim 13, wherein the analyzing data relating to respective pressures of the plurality of comfort layer inflatable members further comprises analyzing data relating to body variances of the person.

15. The method according to claim 13, further comprising:
 analyzing data relating to respective pressures of a plurality of support layer inflatable members that are arranged in the support layer of the sleep support member to generate analyzed support layer data; and
 controlling a pressure of at least one of the support layer inflatable members using the analyzed support layer data.

16. The method according to claim 15, wherein the analyzing data relating to respective pressures of the plurality of support layer inflatable members comprises determining an adjustment to a pressure of at least one of the support layer inflatable members that would cause the sleep support member to provide a more suitable combination of comfort characteristics and support characteristics for the person.

17. The method according to claim 13, wherein the support layer is disposed below the comfort layer.

* * * * *